(12) United States Patent
Park et al.

(10) Patent No.: US 8,273,085 B2
(45) Date of Patent: Sep. 25, 2012

(54) ELECTROSURGICAL INSTRUMENT AND SYSTEM

(75) Inventors: Neil B. Park, Berkshire (GB); Francis Amoah, Berkshire (GB)

(73) Assignee: Gyrus Medical Limited (GB)

(*) Notice: Subject to any disclaimer, the term of this patent is extended or adjusted under 35 U.S.C. 154(b) by 528 days.

(21) Appl. No.: 12/535,082

(22) Filed: Aug. 4, 2009

(65) Prior Publication Data
US 2010/0036371 A1  Feb. 11, 2010

Related U.S. Application Data

(60) Provisional application No. 61/136,191, filed on Aug. 18, 2008.

(30) Foreign Application Priority Data

Aug. 6, 2008 (GB) .................................. 0814424.8

(51) Int. Cl.
*A61B 18/14* (2006.01)
(52) U.S. Cl. ............................................ 606/51; 606/52
(58) Field of Classification Search .............. 606/45–52
See application file for complete search history.

(56) References Cited

U.S. PATENT DOCUMENTS

| | | | |
|---|---|---|---|
| 4,427,006 A | 1/1984 | Nottke | 128/303.14 |
| 5,151,102 A * | 9/1992 | Kamiyama et al. | 606/51 |
| 5,269,780 A | 12/1993 | Roos | 606/42 |
| 5,376,089 A | 12/1994 | Smith | 606/42 |
| 5,573,424 A | 11/1996 | Poppe | 439/502 |
| 5,591,551 A | 1/1997 | Audett et al. | 430/18 |
| 5,658,281 A * | 8/1997 | Heard | 606/48 |
| 5,709,680 A * | 1/1998 | Yates et al. | 606/50 |
| 5,766,166 A | 6/1998 | Hooven | |
| 6,152,923 A | 11/2000 | Ryan | |
| 6,270,497 B1 | 8/2001 | Sekino et al. | 606/42 |
| 6,334,860 B1 * | 1/2002 | Dorn | 606/48 |
| 6,447,511 B1 | 9/2002 | Slater | |

(Continued)

FOREIGN PATENT DOCUMENTS
EP  0 737 447  10/1996
(Continued)

OTHER PUBLICATIONS

International Search Report issued on Aug. 6, 2008 in connection with corresponding PCT application No. PCT/GB2009/001709.

(Continued)

*Primary Examiner* — Michael Peffley
(74) *Attorney, Agent, or Firm* — Ostrolenk Faber LLP

(57) ABSTRACT

An electrosurgical instrument includes a body portion, an actuator, a first jaw having a first electrode and a second jaw. The first electrode has a relatively large area seal surface with a relatively small edge portion and a third electrode, and the second jaw has a second electrode having a relatively large area seal surface and a smaller edge portion. The actuator moves the jaws between an first, open position, a second position for grasping tissue, and a third position where the jaws are further closed such that the first and second seal surfaces are adjacent each other and only the edge portions are exposed. An electrosurgical generator is connected to deliver a coagulation RF waveform between the first and second jaws when in the second position, and to deliver a cutting RF waveform between one or both of the first and second electrodes and the third electrode when the jaw members are in the third position.

15 Claims, 7 Drawing Sheets

U.S. PATENT DOCUMENTS

| | | | |
|---|---|---|---|
| 6,984,231 B2 | 1/2006 | Goble et al. | 606/37 |
| 7,147,637 B2 * | 12/2006 | Goble | 606/50 |
| 7,204,835 B2 | 4/2007 | Latterell et al. | 606/48 |
| 7,442,194 B2 * | 10/2008 | Dumbauld et al. | 606/51 |
| 2003/0163123 A1 * | 8/2003 | Goble et al. | 606/34 |
| 2008/0045947 A1 | 2/2008 | Johnson et al. | |

FOREIGN PATENT DOCUMENTS

| | | |
|---|---|---|
| GB | 2 408 936 | 6/2005 |
| WO | WO 2004/032777 | 4/2004 |
| WO | WO 2008/014103 | 1/2008 |

OTHER PUBLICATIONS

Search Report mailed Nov. 14, 2008 in corresponding United Kingdom Application No. GB 0814424.8.

* cited by examiner

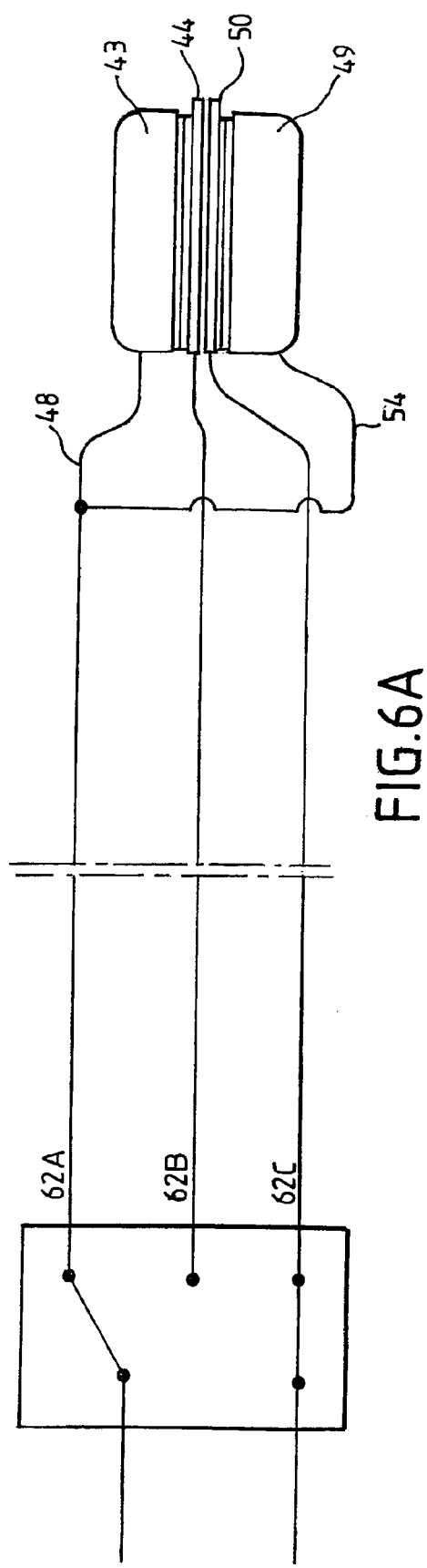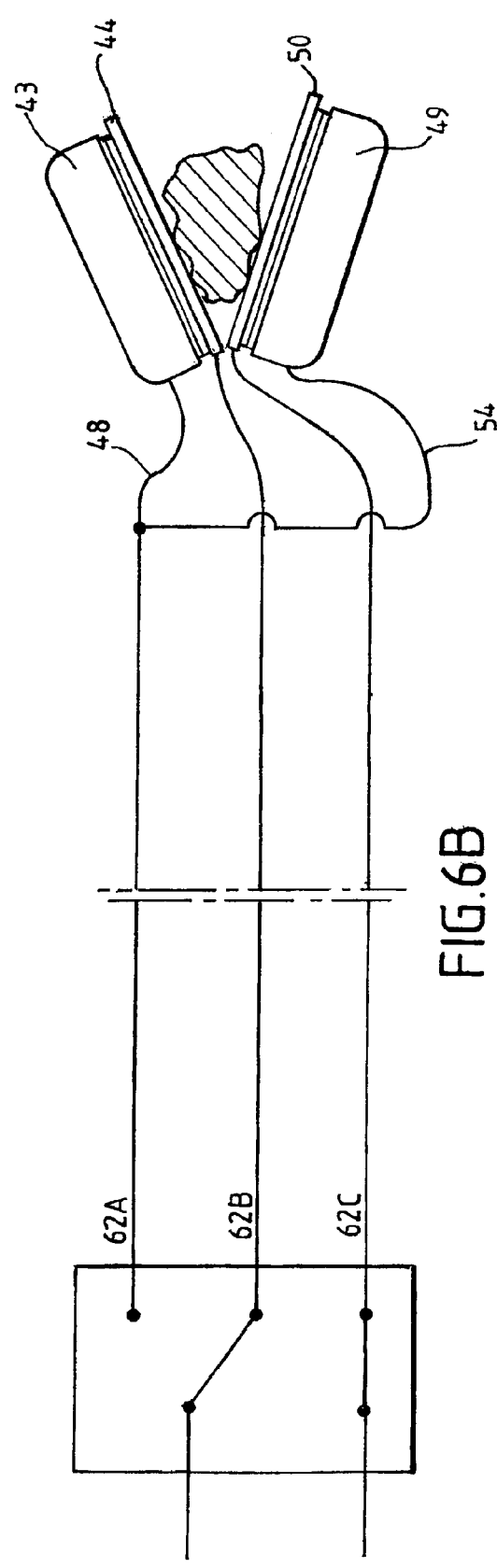

ELECTROSURGICAL INSTRUMENT AND SYSTEM

CROSS-REFERENCE TO RELATED APPLICATION

This application claims the benefit of Provisional Application No. 61/136,191 filed 18 Aug. 2008, the entire contents of which are hereby incorporated by reference in the application.

FIELD OF THE INVENTION

This invention relates to an electrosurgical system comprising a generator and an electrosurgical instrument including electrosurgical electrodes for receiving r.f. power from the generator. Such systems are commonly used for the cutting and/or coagulation of tissue in surgical intervention, most commonly in "keyhole" or minimally invasive surgery, but also in laparoscopic and "open" surgery.

BACKGROUND OF THE INVENTION

It is known to provide electrosurgical generators which provide different radio frequency (RF) power signals for cutting and coagulation, and also to switch between two different instruments, e.g. bipolar and monopolar instruments. In a first type of prior art system, it is also known to provide an electrosurgical instrument with a single electrode, and switching means on the instrument to connect the electrode alternately to either a cutting output or to a coagulating output from the generator. Examples of these types of instrument are to be seen in U.S. Pat. Nos. 4,427,006, 5,376,089 and 5,573,424.

Alternatively, in a second type of prior art system, it is known to provide an instrument with multiple electrodes, and to provide switching means on the instrument to be able to connect the power signal from the generator to different electrodes or combinations of electrodes. Examples of this type of instrument are to be seen in U.S. Pat. Nos. 5,269,780 and 5,951,551. The disadvantage of all of these prior art systems is that it is not possible to optimize both the signal supplied by the generator and the choice of electrodes. In the case of the first type of prior art system, the use of a single electrode means that its design must always be a compromise between designs suited to cutting and those suited to coagulation. In the case of the second type of prior art, the instrument uses the same output power signal from the generator for whichever combination of electrodes is deployed. U.S. Pat. No. 6,270, 497 discloses a device which switches between coagulation and cutting operations, but which is relatively complicated in design.

U.S. Pat. No. 7,204,835 discloses an electrosurgical instrument in which a pair of forceps jaws are provided with a third electrode, designed to effect the electrosurgical cutting of tissue. Such designs have the electrosurgical cutting electrode as a longitudinal rail running along the middle of one of the jaws. An alternative design is shown in U.S. Pat. No. 6,984, 231, which has the electrosurgical cutting electrode as a "nipple" positioned on the outside of one of the jaws.

The present invention attempts to provide an improvement to each of these prior designs, and to provide an instrument capable of effective cutting and coagulation, even in the very restricted spaces encountered in endoscopic surgery.

SUMMARY OF THE INVENTION

Accordingly, there is provided an electrosurgical instrument comprising a body portion, an actuator mechanism associated with the body portion, and first and second jaw member each having a jaw body, the first jaw member including a first electrode having a relatively large area conductive seal surface and a relatively smaller area edge portion, the second jaw member including a second electrode also having a relatively large area conductive seal surface and a relatively smaller area edge portion, the first jaw member comprising a third electrode associated with its jaw body, and an insulator separating the first electrode from the third electrode, operation of the actuator mechanism moving one or both of the first and second jaw members between a first position in which the jaw members are open, a second position in which the first and second jaw members are sufficiently closed so as to be capable of grasping tissue therebetween, and a third position in which the first and second jaw members are further closed such that the conductive seal surfaces on each jaw member are adjacent to one another and such that predominantly the edge portion of at least one the seal surfaces is exposed, the exposed area of the third electrode being greater than that of the exposed edge portion, the electrosurgical instrument also including first, second and third connection elements capable of independently connecting the first, second and third electrodes to an electrosurgical generator.

The instrument is such that when the jaw members of the electrosurgical instrument are in their second position with tissue grasped therebetween, the electrosurgical generator is capable of directing a coagulating RF waveform between the first and second electrodes, and when the jaw members of the electrosurgical instrument are in their third position, the electrosurgical generator is capable of directing a cutting RF waveform between one or both of the first and second electrodes and the third electrode.

In its third position, the jaws are either completely closed, such that the sealing surfaces are in contact with each other, or mostly closed, such that there is a separation of less than 0.2 mm therebetween. In either case, the sealing surfaces are in practice hidden from the tissue to be treated, such that only the edge portions of one or both of the electrodes are exposed to tissue. Unlike the prior art devices, the instrument is not only capable of coagulating tissue grasped between the jaws, but also of cutting tissue in a bipolar manner, with the edge portions of the jaws acting as the active electrode.

In a preferred arrangement, the seal surfaces of the first and second electrodes are such that when the jaw members are in their third position the edge portions of both seal surfaces are exposed. Preferably, the exposed area of the third electrode is at least twice the exposed area of the edge portions of the seal surfaces. This helps to ensure that the narrow edge portions of the first and second electrodes act as the active electrode, and the third electrode acts as the return electrode.

In one convenient arrangement, the third electrode is constituted by the body of the first jaw member, and the insulator spaces apart the first electrode from the body of the first jaw member. Thus, when used in its cutting mode, bipolar energy is conducted through tissue from the edge portions of the first and second electrodes, to the body of one of the jaw members which acts as a return electrode. Alternatively, the third electrode is constituted by the bodies of the first and second jaw members, the bodies of the jaw members being conductive, and wherein a respective insulator member spaces apart each of the first and second electrodes from the associated jaw member body. In this way, energy is transmitted via either or both jaw members.

Typically, the first and second conductive seal surfaces are substantially planar, and the thickness of the first and second electrodes is conveniently between 0.05 and 1.0 mm. The insulator is typically a ceramic layer interposed between the first and third electrodes, conveniently having a thickness of at least 0.2 mm.

The edge portions of the seal surfaces can be flush with the bodies of the jaw members (locally or uniformly). Alternatively, some or all of the edge portion of at least one of the seal surfaces protrudes beyond the periphery of the jaw member. This provides a discontinuity which helps to produce high field intensities and promotes the fire-up of the electrode when cutting tissue. Alternatively or additionally, the edge portion of at least one of the seal surfaces is provided with one or more recessed portions around its periphery. These recesses ensure that only some regions of the periphery of the electrode are in contact with tissue, once again promoting high field intensities in restricted areas and producing effective cutting. As a further addition or alternative, the edge portion of at least one of the seal surfaces is provided with one or more masked portions around its periphery. Once again this ensures that only some regions of the periphery of the electrode are in contact with tissue, promoting high field intensities in restricted areas and producing effective cutting.

The electrosurgical instrument is specifically suitable for endoluminal surgical applications and in particular for gastrointestinal surgery. The narrow diameter and generally slim-line construction makes the instrument ideal for endoluminal applications, or for paediatric surgery where surgical access is even more difficult.

The electrosurgical instrument operates with different electrodes activated depending on whether the instrument is used to coagulate tissue or cut tissue. Where the instrument is being used to coagulate tissue, the first and second electrodes are activated so that tissue is coagulated between the conductive sealing surfaces of the first and second jaw members. Where the instrument is being used to cut tissue, the bipolar signal is provided not between the first and second electrodes, but between one or both of the first and second electrodes and the third electrode.

Accordingly, the invention further resides in an electrosurgical system including an electrosurgical instrument and an electrosurgical generator, the electrosurgical instrument comprising a body portion, an actuator mechanism associated with the body portion, and first and second jaw members each having a jaw body, the first jaw member including a first electrode having a relatively large area conductive seal surface and a relatively smaller area edge portion, the second jaw member including a second electrode also having a relatively large area conductive seal surface and a relatively smaller area edge portion, the first jaw member comprising a third electrode associated with its jaw body, and an insulator separating the first electrode from the third electrode, operation of the actuator mechanism moving one or s both of the first and second jaw members between a first position in which the jaw members are open, a second position in which the first and second jaw members are sufficiently closed so as to be capable of grasping tissue therebetween, and a third position in which the first and second jaw members are further closed such that the conductive seal surfaces on each jaw member are adjacent to one another other such that predominantly the edge portions of the seal surfaces are exposed, the electrosurgical generator including a source of radio frequency energy capable of producing either a coagulating RF waveform or a cutting RF waveform, and first second and third output connections connected to the first, second and third electrodes respectively of the electrosurgical instrument, the generator further including a switching means, and a controller, the controller being such that when the jaw members of the electrosurgical instrument arc in their second position with tissue grasped therebetween, the switching means directs the coagulating RF waveform between the first and second output connections and hence the first and second electrodes, and when the jaw members of the electrosurgical instrument are in their third position, the switching means directs the cutting RF waveform between one or both of the first and second electrodes and the third electrode.

As before, the exposed area of the third electrode is conveniently greater than that of the exposed edge portions, preferably by at least twice as much.

BRIEF DESCRIPTION OF THE DRAWINGS

The invention will now be further described, by way of example only, with reference to the accompanying drawings, in which.

DESCRIPTION OF PREFERRED EMBODIMENTS

Figure 1:
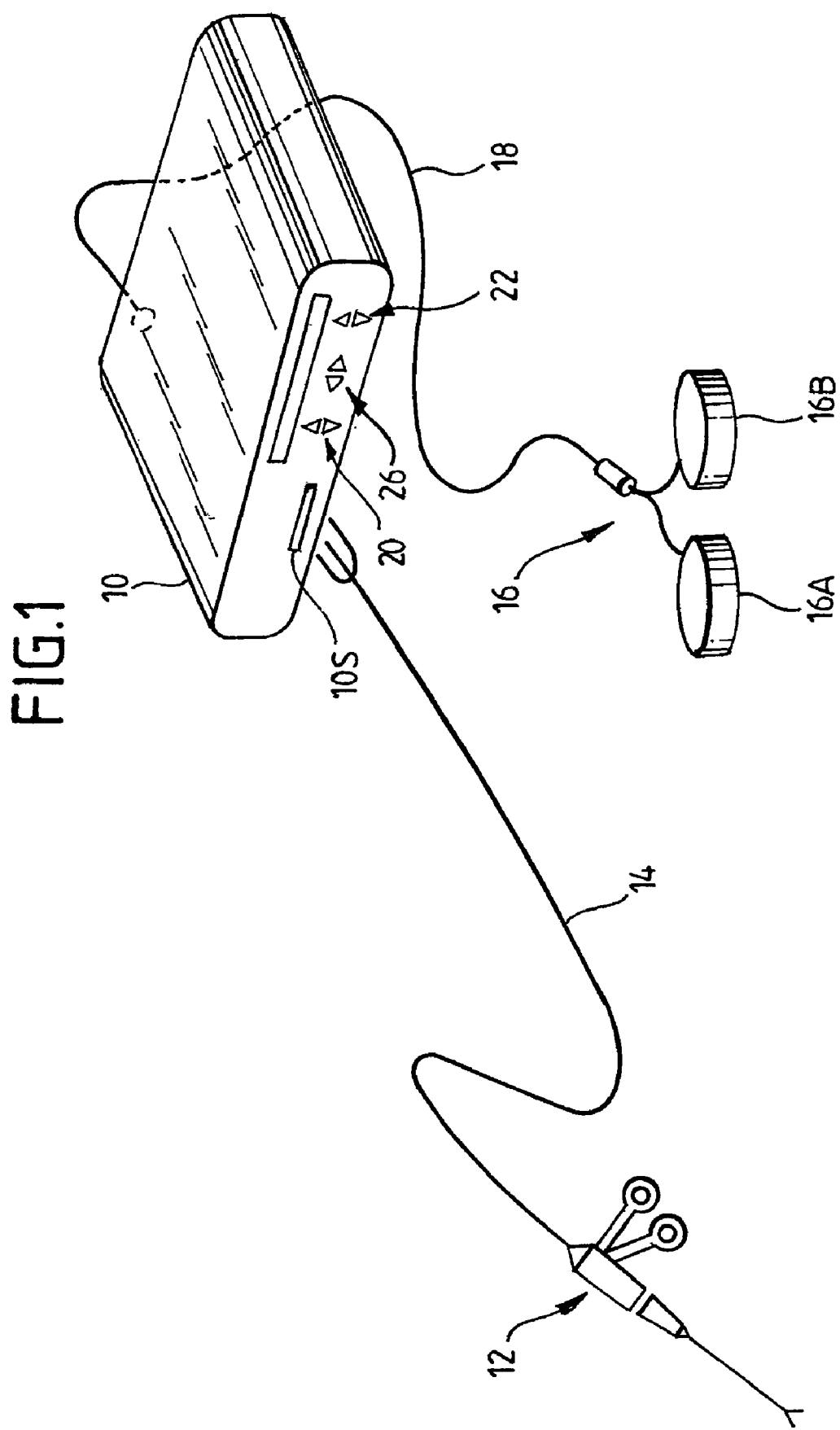
FIG. 1 is a schematic diagram of an electrosurgical system.

Referring to FIG. 1, a generator 10 has an output socket 10S providing a radio frequency (RF) output for an instrument 12 via a connection cord 14. Activation of the generator may be performed from the instrument 12 via a connection in cord 14 or by means of a footswitch unit 16, as shown, connected to the rear of the generator by a footswitch connection cord 18. In the illustrated embodiment footswitch unit 16 has two footswitches 16A and 16B for selecting a coagulation mode and a cutting mode of the generator respectively. The generator front panel has push buttons 20 and 22 for respectively setting coagulation and cutting power levels, which are indicated in a display 24. Push buttons 26 are provided as an alternative means for selection between coagulation and cutting modes.

Figure 2:
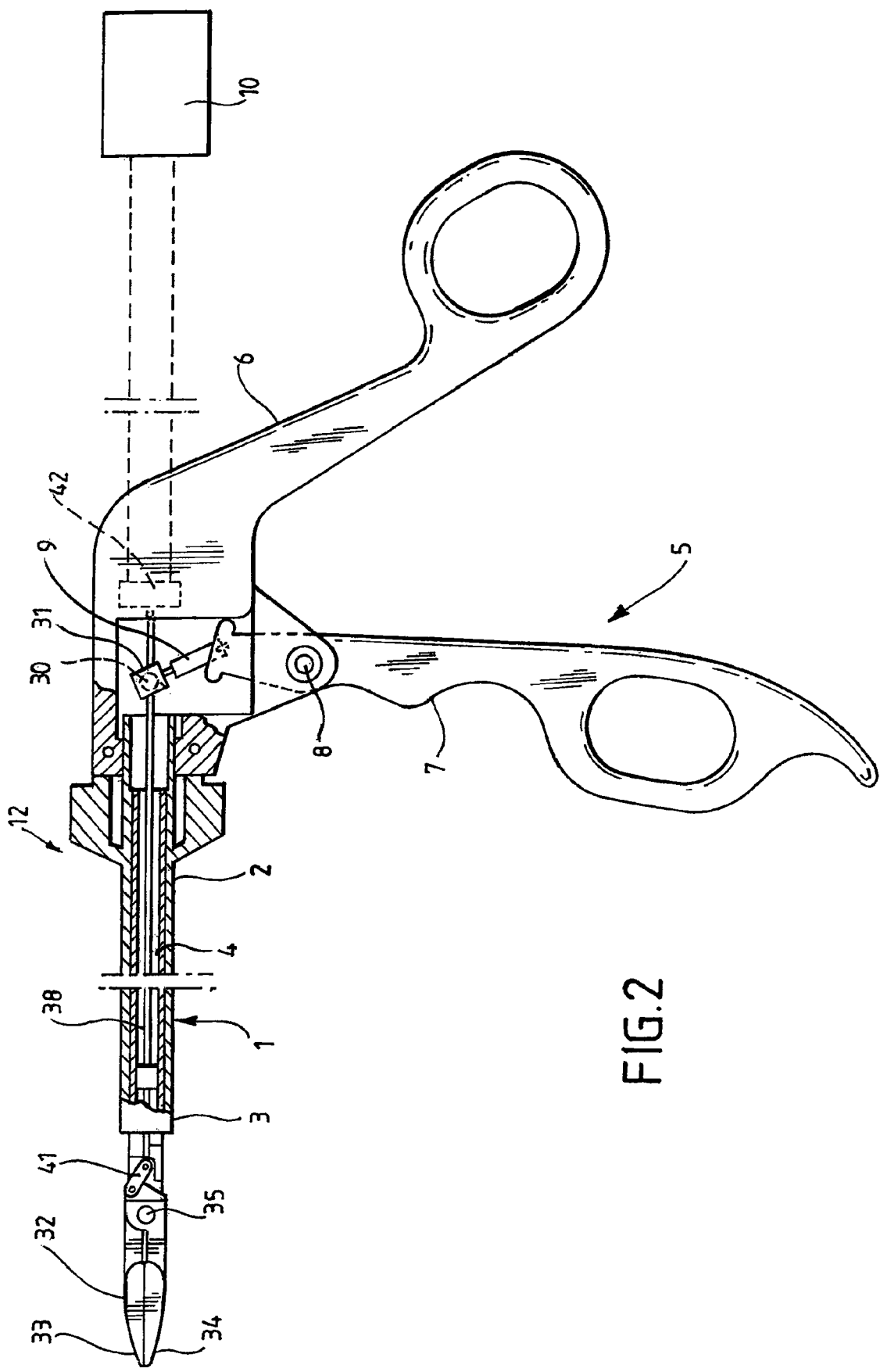
FIG. 2 is a schematic side view, shown partly in section, of a forceps-type instrument for use in the system of FIG. 1.

FIG. 2 shows an embodiment of the instrument 12 in more detail. The instrument 12 is a bipolar forceps device including an elongated tubular shaft 1 with a proximal end 2, distal end 3, and a lumen 4 which extends for the entire length of the tubular member. At the proximal end 2 of the tubular member 1 is a scissors-type handle assembly 5 with a first handle 6 and a second handle 7. The second handle 7 is pivotable with respect to the first, about pivot pin 8. In a known design of actuation mechanism, the second handle 7 has a pin 9 affixed to the top thereof, such that movement of the handle causes a corresponding movement to a sphere 30 supported in a U-shaped cradle 31.

Figure 3:
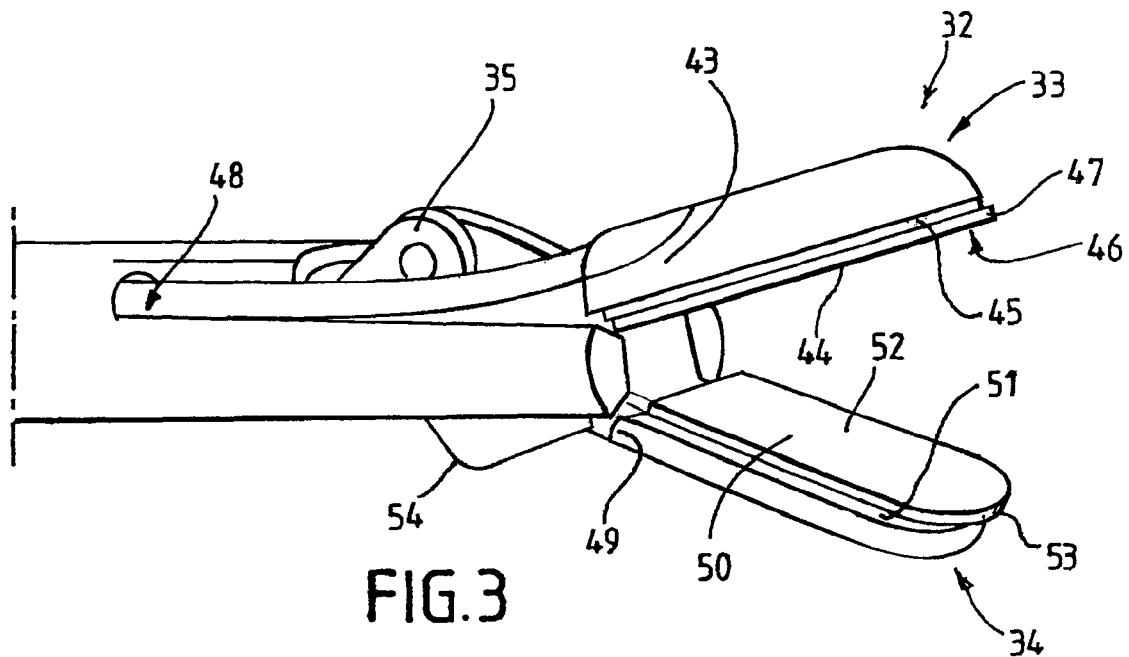
FIG. 3 is an enlarged perspective view of the end effector of the instrument of FIG. 2, shown in its open position.
Figure 4:
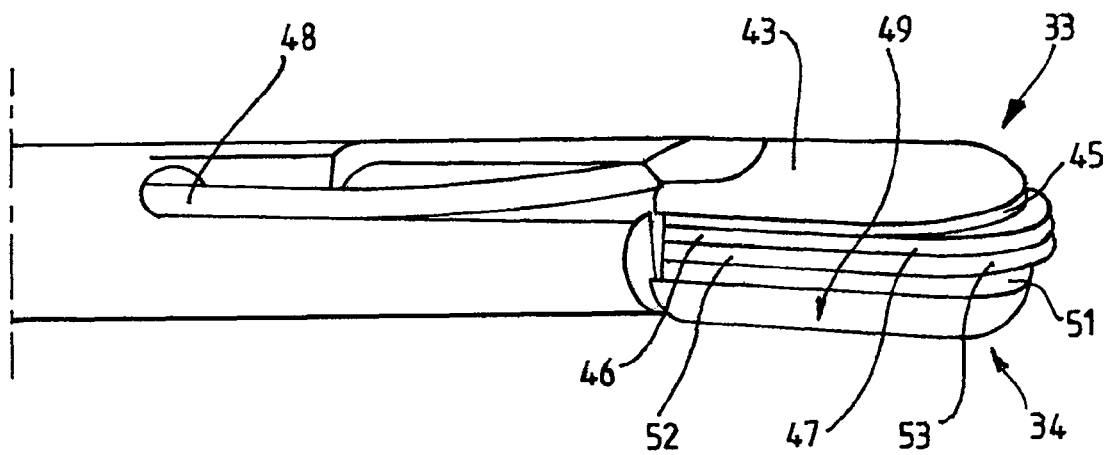
FIG. 4 is an enlarged perspective view of the end effector of the instrument of FIG. 2, shown in its closed position.

Fitted into the distal end 3 of the tubular member 1 is a forceps jaw assembly 32, more particularly shown in FIGS. 3 and 4. The jaw assembly 32 comprises a first jaw member 33 and a second jaw member 34, pivotally joined to each other by an insulated rivet 35. The jaw assembly 32 is opened and closed by means of a push rod 38, extending through the lumen 4 of the tubular member 1. The rod 38 is pivotally connected to the jaw members 33, 34 by rigid links 41. The proximal ends of the rod 38 extend from the tubular member through the sphere 30 and terminate in a connector 42, by which means the device can be attached to the electrosurgical generator 10.

Although a "laparoscopic-type" handle is illustrated in FIG. 2, a "resectoscope-type" handle can also be used with the instrument. Both of such types of handle will be well known to those skilled in the art of minimally invasive surgery.

FIGS. 3 and 4 show the jaw assembly 32 in more detail. The first jaw member 33 comprises a conductive jaw body 43 and a conductive sealing plate 44, separated by a ceramic insulating layer 45. The sealing plate 44 has a planar sealing surface 46 and edge portions 47 around the periphery thereof. Although shown with a generally smooth surface in FIG. 3, the sealing surface 46 can be provided with a roughened surface or even serrated to assist in the gripping of tissue. The conductive jaw body 43 is connected to one output connection of the generator 10 by means of lead 48 and connector 42. The conductive sealing plate 44 is connected to a different output connection of the generator 10 by means of connector 42 and lead (not shown).

The second jaw member 34 has a similar construction, with a conductive jaw body 49 and a conductive sealing plate 50, separated by a ceramic insulating layer 51. The sealing plate 50 has a planar sealing surface 52 and edge portions 53 around the periphery thereof. The conductive jaw body 49 is connected to one output connection of the generator 10 by means of lead 54 and connector 42. The conductive sealing plate 50 is connected to a different output connection of the generator 10 by means of connector 42 and lead (not shown).

In use the instrument 12 is introduced into the surgical site in the closed position shown in FIG. 4, so that the cross-sectional area of the instrument tip is as small as possible. Once at the surgical site, to coagulate tissue, the jaw members 33, 34 are opened and the jaw assembly 32 is manoeuvred so that tissue is constrained between the jaw members 33, 34. The handle assembly 5 is operated to close the jaw assembly 32 such that the tissue is grasped firmly between the first and second jaw members 33, 34. The generator 10 is then activated so as to send a coagulating RF waveform between the sealing plate 44 on the first jaw member, and the sealing plate 50 on the second jaw member. The RF energy is transmitted to the tissue via the sealing surfaces 46, 52, and the tissue becomes coagulated.

When it is desired to cut tissue at the surgical site, the operation of the instrument 12 is somewhat different. The jaw assembly 32 is closed as shown in FIG. 4, so that the sealing surfaces 46 and 52 are hidden, and only the edge portions 47, 53 are exposed to tissue. The edge portions 47, 53 protrude slightly beyond the periphery of the jaw members 33, 34 as shown in FIG. 4. In cutting mode, the electrosurgical generator switches the active output connections so that a cutting RF waveform is no longer delivered between the first and second sealing plates as in the coagulation of tissue. In cutting mode, one pole of the generator 10 is connected to the conductive jaw bodies 43, 49 of the first and second jaw members respectively. The other pole of the electrosurgical generator is connected to the first and second sealing plates 44, 50, which are commonly connected due to the contact between the sealing surfaces 46 & 52. In this way, a bipolar cutting waveform is delivered to tissue, with the exposed edge portions 47, 53 constituting the active electrode and the jaw bodies 43, 49 constituting the return electrode. Due to the fact that the exposed surface area of the edge portions is much less than that of the conductive jaw bodies, the edge portions will assume the role of the active electrode and the jaw bodies the role of the return electrode. Thus tissue can be cut by moving the edge of the jaw assembly against the tissue, and coagulated by grasping the tissue between the jaws.

It is not necessary that the jaw members 33, 34 be completely closed in order to cut tissue, as long as the majority of the sealing surfaces 46, 52 are hidden from the tissue. A separation of 0.2 mm or less has been found to be sufficient for effective tissue cutting.

Figure 5:
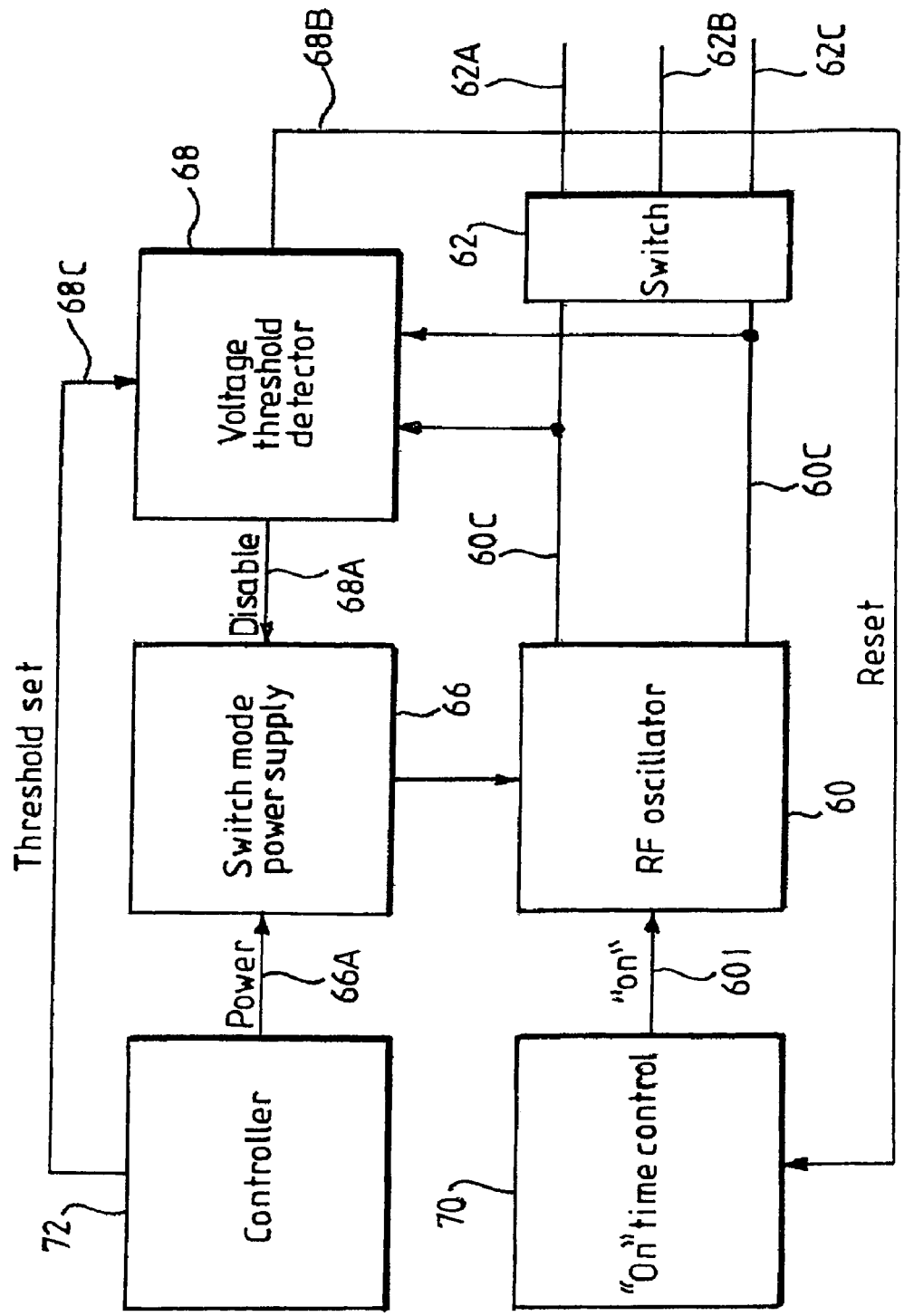
FIG. 5 is a block diagram of a generator forming part of the system of FIG. 1, FIGS. 6A and 6B are schematic circuit diagrams of the instrument of FIG. 2, including switching circuitry and shown in first and second alternative conditions.

FIG. 5 shows how the generator 10 switches to provide the coagulating and cutting RF waveforms to different electrodes. The generator 10 comprises a radio frequency (RF) output stage in the form of a power oscillator 60 having a pair of output lines 60C for coupling via switching circuit 62 to the instrument 12. Switching circuit 62 has three output connections 62A, 62B and 62C for connection to the electrodes of the instrument 12. Power is supplied to the oscillator 60 by a switched mode power supply 66.

In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output lines 60C is a voltage threshold detector 68 having a first output 68A coupled to the switched mode power supply 16 and a second output 68B coupled to an "on" time control circuit 70. A micro-processor controller 72 coupled to the operator controls and display (shown in FIG. 1) is connected to a control input 66A of the power supply 66 for adjusting the generator output power by supply voltage variation and to a threshold-set input 68C of the voltage threshold detector 68 for setting peak RF output voltage limits.

In operation, the microprocessor controller 72 causes power to be applied to the switched mode power supply 66 when electrosurgical power is demanded by the surgeon operating an activation switch arrangement which may be provided on a hand-piece or footswitch (see FIG. 1). A constant output voltage threshold is set independently of the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved.

When the generator is first activated, the status of the control input 60I of the RF oscillator 60 (which is connected to the "on" time control circuit 70) is "on", such that the power switching device which forms the oscillating element of the oscillator 60 is switched on for a maximum conduction period during each RF oscillation cycle. The power delivered to the load 64 depends partly on the supply voltage applied to the RF oscillator 60 from the switched mode power supply 66 and partly on the load impedance 64. The voltage threshold for a desiccation output is set to cause trigger signals to be sent to the "on" time control circuit 70 and to the switched mode power supply 66 when the voltage threshold is reached. The "on" time control circuit 70 has the effect of virtually instantaneously reducing the "on" time of the RF oscillator-switching device. Simultaneously, the switched mode power supply is disabled so that the voltage supplied to oscillator 60 begins to fall. The operation of the generator in this way is described in detail in our European Patent Application No. 0754437, the disclosure of which is hereby incorporated by way of reference.

The operation of the generator 10 will now be described with reference to FIGS. 6A and 6B. Output connection 62A is commonly connected to both of the conductive jaw bodies 43 and 49. Output connection 62B is connected to sealing plate 44, while output connection 62C is connected to sealing plate 50. When it is desired to operate the instrument 12 in a cutting mode, footswitch 16A is depressed which causes a signal to be sent to the controller 72 which sets the switching circuit 62 to its "cut" position. This is illustrated in FIG. 6A, in which the signals from the oscillator 60 are connected between output connections 62A and 62C. This means that the RF power signal is applied between the sealing plate 50 (via output connection 62C) and the conductive jaw bodies 43 and 49 (via output connection 62A). Output connection 62B (and hence sealing plate 44) has no direct connection to the generator, but is connected to the sealing plate 50 and hence output connection 62C by virtue of the two sealing plates being in contact one with the other.

At the same time as the controller 72 sets the switching circuit to the position in FIG. 6A, it also sends a signal via line 68C to the voltage threshold detector 68 to set the peak output voltage limit to a relatively high "cutting" level. The control of this cutting signal is described in more detail in EP 0754437, referred to earlier. In cutting mode, the output from the generator is a relatively high voltage, with a consequent low current level, with the RF cutting voltage being supplied between the two sealing plates and the two jaw bodies, so that tissue may be cut by the edge portions of the jaw assembly 32.

Alternatively, when it is desired to operate the instrument 12 in a coagulation mode, footswitch 16B is depressed which causes the controller 72 to set the switching circuit 62 to its "coag" state, as illustrated in FIG. 6B. In this set-up, the power signals from the oscillator are connected between output connections 62B and 62C. This means that the RF power signal is applied between the two sealing plates 44 and 50. Output connection 62A and hence the two jaw bodies are disconnected from the generator. At the same time the controller sends a signal to the voltage threshold detector 68 to set the peak output voltage limit to a relatively lower "coagulating" level, again as more particularly described in EP 0754437. In "coag" mode, the output from the generator is a relatively lower voltage, with a corresponding relatively higher current. The voltage differential between the sealing plates 44 and 50 permits the coagulation of tissue held by the jaw assembly 32.

Figure 7:
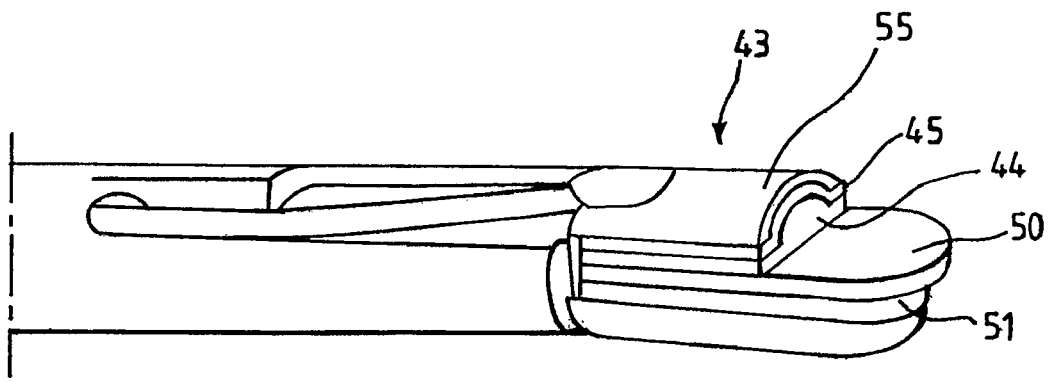
FIG. 7 is an enlarged perspective view of an alternative embodiment of end effector, shown partly in section.

Alternative embodiments of the instrument 12 are envisaged in which the construction of the jaw members varies slightly. FIG. 7 shows an arrangement in which the third electrode is not constituted by the whole of the body of the jaw body 43, but by a separate conductive layer 55. Conductive layer 55 is separated from the sealing plate 44 by insulating layer 45 as before, but in this construction the bulk of the jaw body is constituted by the sealing plate 44 as opposed to the jaw body 43 as in the embodiment of FIG. 3. Alternatively, the bulk of the jaw member could be made of an insulating material, with both the sealing plate 44 and the conductive layer 55 being relatively thin layers applied on opposite sides of the insulating jaw material. Conceivably, the insulating material could comprise multiple layers of similar or dissimilar materials, such as silicones or ceramics.

Figure 8:
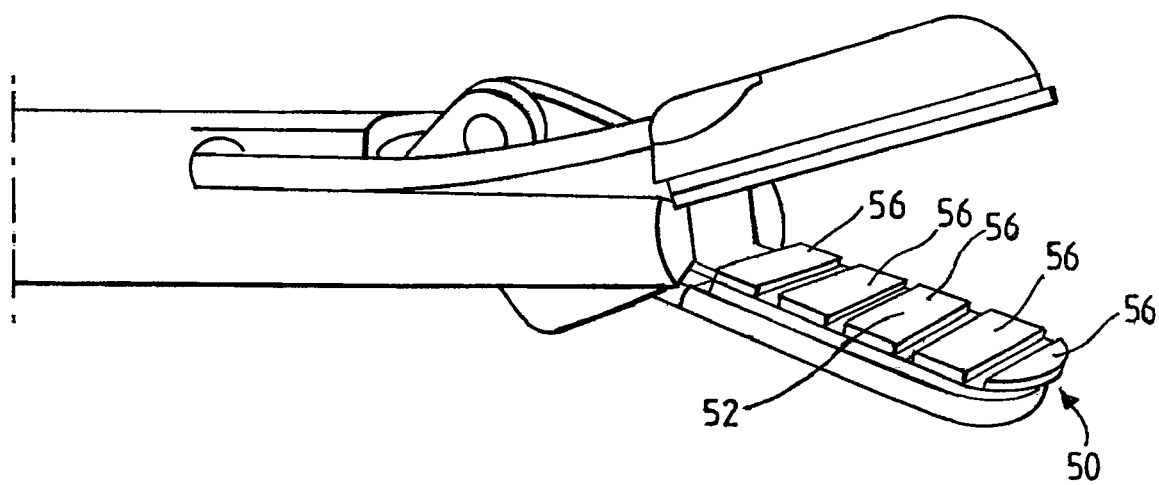
FIGS. 8 to 11 are enlarged perspective views of further alternative embodiments of end effector.

FIG. 8 shows an embodiment in which the sealing plate 50 is constituted by means of a plurality of separate sub-plates 56. These can be commonly energized, or alternatively each sub-plate 56 can be independently connected so as to be able to be separately energized during the coagulation process. This enables increased control of the coagulation process, as separate areas of the overall sealing surface 52 can be energized in sequence, or in response to some feedback control (e.g. of tissue impedance) during the coagulation process.

Figure 9:
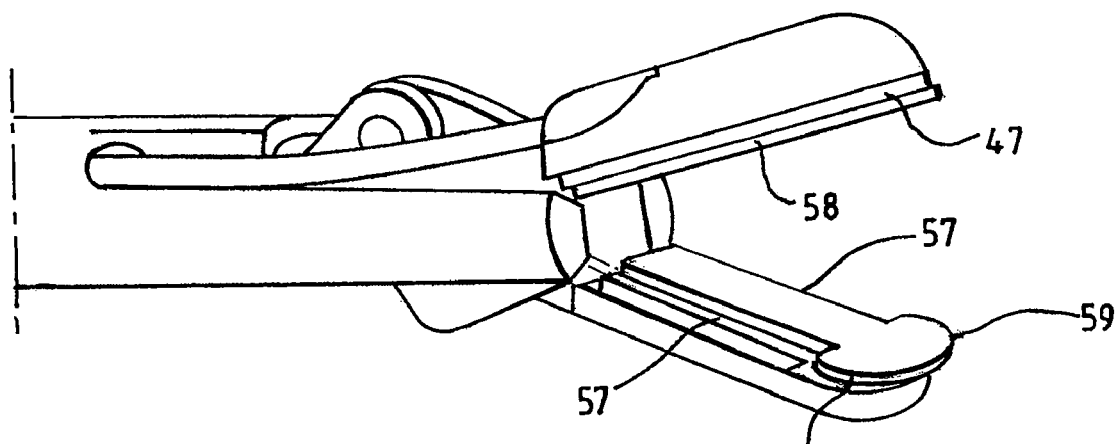
Figure 10:
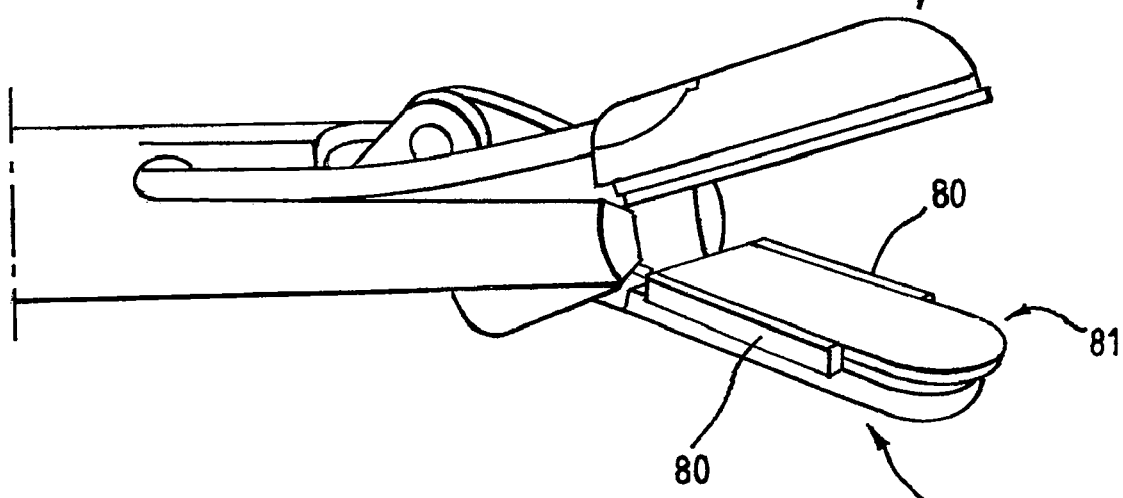

FIG. 9 shows an embodiment in which the sealing plates 44, 50 are each provided with recessed portions 57, 58 respectively. This limits the contact in the tissue-cutting mode between the edge portions 47, 53 and the tissue to a smaller area 59 towards the tip of the jaw members. This design concentrates the cutting action to a smaller area to allow for the more precise control of the cutting process, and also produces more intense cutting due to the higher electric field intensities produced by the smaller tissue-contacting area. In the same way, FIG. 10 shows an embodiment in which insulating runners 80 are present along the edge portion 53, in order to limit the conductive areas of the edge portion to a smaller tip area 81. The effect will be the same, namely to provide a smaller, more intense cutting area, allowing for greater control and a more effective cutting action.

Figure 11:
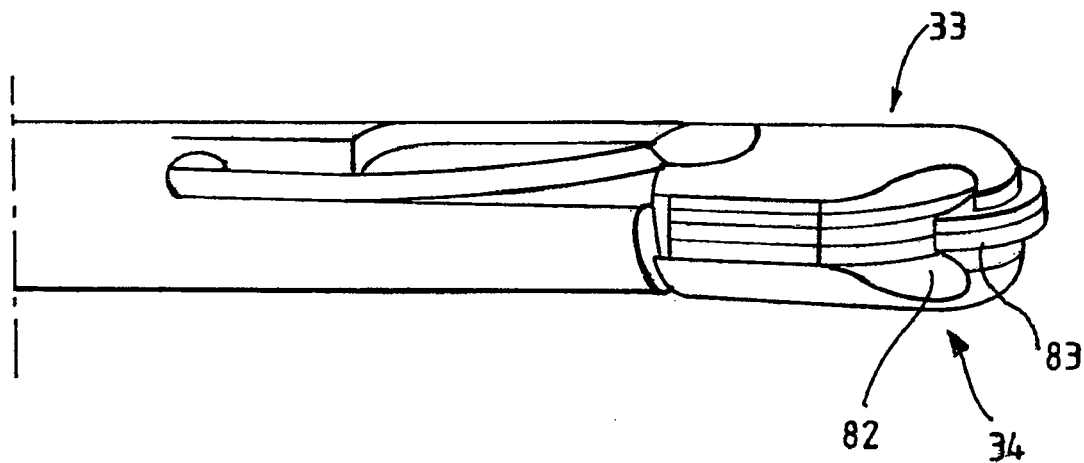

Finally, FIG. 11 shows a further embodiment in which the profile of both jaws has been altered, to provide a generally hook-shaped end effector. Both jaw members 33, 34 are shaped with a recessed portion 82 defining a hook portion 83 towards the distal end of the jaw assembly 32. The jaw members 33, 34 can still open and close to coagulate tissue therebetween, but when they are in their closed position they can cut tissue with a retrograde action in which the instrument 12 is pulled proximally towards the user. This is particularly useful in dissecting tissue and severing relatively thin vessels and fronds of tissue.

Generally, it will be appreciated that other embodiments of the generator and the jaw members can be envisioned without departing from the scope of the present invention. By employing three or more electrodes and selecting their coupling to the source of the RF power, and also adjusting the RF power signal depending on which electrodes are being employed at any one time, the electrosurgical signal and the electrode configuration can be matched to optimum effect.

The invention claimed is:
1. An electrosurgical instrument comprising:
a body portion,
an actuator mechanism associated with the body portion, and
first and second jaw members each having a jaw body,
the first jaw member including a first electrode having a relatively large area conductive seal surface and a relatively smaller area conductive edge portion,
the second jaw member including a second electrode also having a relatively large area conductive seal surface and a relatively smaller area conductive edge portion,
the first jaw member comprising:
a third electrode associated with its jaw body, and having a conductive exposed surface area, and an insulator separating the first electrode from the third electrode,
the actuator mechanism being configured to provide an operation of moving one or both of the first and second jaw members between a first position in which the jaw members are open, a second position in which the first and second jaw members are sufficiently closed so as to be capable of grasping tissue therebetween, and a third position in which the first and second jaw members are further closed such that the conductive seal surfaces on each jaw member are adjacent to one another and such that predominantly the conductive edge portion of one or both of the seal surfaces is exposed, the conductive exposed area of the third electrode being greater than that of the conductive exposed edge portion, the electrosurgical instrument also including first, second and third connection elements capable of independently connecting the first, second and third electrodes to an electrosurgical generator.

2. An electrosurgical instrument according to claim 1, wherein the exposed area of the third electrode is at least twice the exposed area of the edge portion of the seal surfaces.

3. An electrosurgical instrument according to claim 1, wherein the third electrode is constituted by the body of the first jaw member, the first jaw member body being conductive, and the insulator spaces apart the first electrode from the body of the first jaw member.

4. An electrosurgical instrument according to claim 1, wherein the third electrode is constituted by the bodies of the first and second jaw members, the bodies of the jaw members being conductive, and wherein a respective insulator member spaces apart each of the first and second electrodes from the associated jaw member body.

5. An electro surgical instrument according to claim 1, wherein the first and second conductive seal surfaces are substantially planar.

6. An electrosurgical instrument according to claim 5, wherein the thickness of each of the first and second electrodes is between 0.05 and 1.0 mm.

7. An electrosurgical instrument according to claim 4, wherein each insulator member is a ceramic layer interposed respectively between the first or second electrode and the associated first or second jaw member body.

8. An electrosurgical instrument according to claim 7, wherein the thickness of the ceramic layer is greater than or equal to 0.2 mm.

9. An electrosurgical instrument according to claim 1, wherein some or all of the edge portion of at least one of the seal surfaces protrudes beyond the periphery of the associated jaw member body.

10. An electrosurgical instrument according to claim 1, wherein the edge portion of at least one of the seal surfaces is provided with one or more recessed portions around its periphery.

11. An electrosurgical instrument according to claim 1, wherein the edge portion of at least one of the seal surfaces is provided with one or more masked portions around its periphery.

12. An electrosurgical instrument according to claim 1, wherein the seal surfaces of the first and second electrodes are such that when the jaw members are in their third position the edge portions of both seal surfaces are exposed.

13. An electrosurgical system including an electrosurgical instrument and an electrosurgical generator, the electrosurgical instrument comprising:
 a body portion,
 an actuator mechanism associated with the body portion, and
 first and second jaw members each having a jaw body,
  the first jaw member including a first electrode having a relatively large area conductive seal surface and a relatively smaller area conductive edge portion,
  the second jaw member including a second electrode also having a relatively large area conductive seal surface and a relatively smaller area conductive edge portion,
  the first jaw member comprising:
   a third electrode associated with its jaw body, and having a conductive exposed surface area, and an insulator separating the first electrode from the third electrode,
 the actuator mechanism being configured to provide an operation of moving one or both of the first and second jaw members between a first position in which the jaw members are open, a second position in which the first and second jaw members are sufficiently closed so as to be capable of grasping tissue therebetween, and a third position in which the first and second jaw members are further closed such that the conductive seal surfaces on each jaw member are adjacent to one another such that predominantly the conductive edge portion of one or both of the seal surfaces is exposed,
 the electrosurgical generator including a source of radio frequency energy configured to produce either a coagulating RF waveform or a cutting RF waveform, and first, second and third output connections connected to the first, second and third electrodes respectively of the electrosurgical instrument,
 the generator further including a switching means, and a controller, the controller being configured such that when the jaw members of the electrosurgical instrument are in their second position with tissue grasped therebetween, the switching means directs the coagulating RF waveform between the first and second output connections and hence the first and second electrodes, and when the jaw members of the electrosurgical instrument are in their third position, the switching means directs the cutting RF waveform between one or both of the first and second electrodes and the third electrode, such that the conductive edge portions of one or both of the seal surfaces can act as a cutting electrode and the third electrode can act as a return electrode for the cutting electrode.

14. An electrosurgical system according to claim 13, wherein the exposed area of the third electrode is greater than that of the exposed edge portions.

15. An electrosurgical instrument comprising:
 a body portion,
 first and second jaw members, and,
 associated with the body portion, an actuator mechanism coupled to at least one of the jaw members and configured to move that jaw member relative to the other jaw member, wherein:
 the first jaw member and the second jaw member respectively include a first electrode and a second electrode each having a respective conductive seal surface and an insulative backing, the seal surfaces facing each other so as to lie adjacent one other when the jaw members are in a closed configuration;
 the first jaw member includes a third electrode which is insulated from the first electrode by the insulative backing of the first jaw member and which is exposed when the jaw members are in their closed configuration;
 at least one of the first and second electrodes has a laterally directed conductive edge portion that remains exposed when the jaw members are in their closed configuration, the exposed surface area being relatively small compared with the area of the conductive seal surface of the at least one electrode; and
 the instrument also includes first, second and third connection elements allowing independent connection of the first, second and third electrodes to a radio frequency (RF) electrosurgical generator.

* * * * *